United States Patent
Dorton (10) Patent No.: US 11,399,469 B2
(45) Date of Patent: Aug. 2, 2022

(54) ORIGINAL CLONE CUTTER

(71) Applicant: Chad Eric Dorton, Acton, CA (US)

(72) Inventor: Chad Eric Dorton, Acton, CA (US)

( * ) Notice: Subject to any disclaimer, the term of this patent is extended or adjusted under 35 U.S.C. 154(b) by 0 days.

(21) Appl. No.: 17/061,277

(22) Filed: Oct. 1, 2020

(65) Prior Publication Data

US 2021/0015051 A1 Jan. 21, 2021

Related U.S. Application Data (63) Continuation-in-part of application No. 16/001,906, filed on Jun. 6, 2018, now abandoned.
(60) Provisional application No. 62/603,625, filed on Jun. 6, 2017.

(51) Int. Cl.
| | | |
|---|---|---|
| *A01G 2/10* | (2018.01) | |
| *A01H 4/00* | (2006.01) | |
| *A01G 3/02* | (2006.01) | |

(52) U.S. Cl.
CPC .............. *A01G 2/10* (2018.02); *A01G 3/02* (2013.01); *A01H 4/005* (2013.01)

(58) Field of Classification Search
CPC ... A01G 3/02; A01G 2/10; A01G 2/35; A01H 4/005
See application file for complete search history.

(56) References Cited

U.S. PATENT DOCUMENTS

| | | |
|---|---|---|
| 57,553 A | 8/1866 | Neff, Jr. |
| 98,840 A | 1/1870 | Barnard |
| 238,080 A | 2/1881 | Venavides et al. |
| 240,953 A | 5/1881 | Bogard |
| 258,089 A | 5/1882 | Mann |
| 415,216 A | 11/1889 | McDonough |
| 477,952 A | 6/1892 | Jory |
| 519,999 A | 5/1894 | Godbey |
| 541,862 A | 7/1895 | Lohlein |
| 594,072 A | 11/1897 | Forde |
| 628,483 A | 7/1899 | Macri |
| 654,008 A | 7/1900 | Kirkland |
| 770,347 A | 9/1904 | Brown |
| 846,732 A | 3/1907 | Deshane |
| 849,252 A | 4/1907 | Lipscomb |
| 875,717 A | 1/1908 | Low |
| 1,082,400 A | 12/1913 | Burnite |
| 1,299,104 A | 4/1919 | Arnold |
| 1,847,401 A | 3/1932 | Klein |
| D115,932 S | 8/1939 | Larocque |
| 2,254,738 A | 9/1941 | Gamache |
| 2,320,460 A | 6/1943 | Müller |
| 2,612,686 A | 10/1952 | Wagner |
| 2,681,504 A | 6/1954 | Fox |
| 2,775,032 A | 12/1956 | Sorensen |
| D194,049 S | 11/1962 | Harano |
| 3,336,667 A | 8/1967 | Wallace et al. |
| 3,407,498 A | 10/1968 | Young |

(Continued)

*Primary Examiner* — Sean M Michalski
(74) *Attorney, Agent, or Firm* — Troutman Pepper Hamilton Sanders LLP (57) ABSTRACT

The present invention is a single blade clone cutter. The single blade clone cutter comprises a u-shaped housing with a single removable blade. The blade is locked into the u-shaped housing to secure the blade from moving during the process of cutting. It is important to have a single blade that cuts onto a flat surface so there is no damage being done to the fibers at the end of a cutting.

9 Claims, 6 Drawing Sheets

(56) References Cited

U.S. PATENT DOCUMENTS

| | | |
|---|---|---|
| 3,548,496 A | 12/1970 | Van Hook |
| 3,608,196 A | 9/1971 | Wiss |
| 3,659,343 A | 5/1972 | Straus |
| D228,868 S | 10/1973 | Bush |
| 3,972,333 A | 8/1976 | Leveen |
| 4,053,979 A | 10/1977 | Tuthill et al. |
| 4,092,776 A | 6/1978 | Ferguson |
| D255,763 S | 7/1980 | Ferguson |
| D263,350 S | 3/1982 | Gingher, Jr. |
| D264,018 S | 4/1982 | Gingher, Jr. |
| D269,820 S | 7/1983 | Bisson |
| D273,172 S | 3/1984 | Yamagishi |
| D276,786 S | 12/1984 | Chen |
| 4,581,823 A | 4/1986 | Gilman |
| 4,711,031 A | 12/1987 | Annello |
| D296,042 S | 6/1988 | Lee |
| D303,872 S | 10/1989 | Tamamura |
| 4,902,776 A | 2/1990 | Hirai et al. |
| 4,987,682 A | 1/1991 | Minnick |
| 5,007,171 A | 4/1991 | Horning, Jr. |
| 5,016,353 A | 5/1991 | Iten |
| D317,390 S | 6/1991 | Iharasgu |
| 5,117,524 A * | 6/1992 | Chang .................... B43M 7/002 30/123 |
| 5,117,557 A | 6/1992 | Hartley |
| 5,127,161 A * | 7/1992 | Ikeda .................... B43M 7/002 30/294 |
| 5,226,236 A | 7/1993 | Harrington, III |
| D340,854 S | 11/1993 | Shimoharaguchi |
| 5,348,759 A | 9/1994 | Weaver et al. |
| 5,353,505 A | 10/1994 | Okada |
| 5,438,759 A | 8/1995 | Dieringer |
| 5,471,745 A | 12/1995 | Wendell |
| 5,507,096 A | 4/1996 | Gamba |
| 5,711,075 A | 1/1998 | Wolf |
| 5,964,033 A | 10/1999 | Wolf |
| 6,000,136 A | 12/1999 | Owens |
| 6,317,987 B1 | 11/2001 | Joung |
| 6,578,243 B1 | 6/2003 | Hall |
| D485,014 S | 1/2004 | LaManga et al. |
| D503,323 S | 3/2005 | Hasegawa et al. |
| 7,073,264 B2 | 7/2006 | Votolato |
| 7,314,471 B2 | 1/2008 | Holman |
| D576,846 S | 9/2008 | Holcomb et al. |
| D613,571 S | 4/2010 | Quante |
| 7,730,620 B1 | 6/2010 | Anastasi |
| D625,978 S | 10/2010 | Zeng |
| D639,126 S | 6/2011 | Wu |
| 8,429,825 B2 | 4/2013 | Johanson |
| 8,607,677 B2 | 12/2013 | Nelson et al. |
| 8,819,941 B2 | 9/2014 | Mensch |
| 8,869,407 B2 | 10/2014 | Votolato |
| 8,869,408 B2 | 10/2014 | Votolato |
| D720,696 S | 1/2015 | Huang |
| D720,969 S | 1/2015 | Lipscomb et al. |
| 8,984,754 B1 | 3/2015 | Kaidi et al. |
| D736,050 S | 8/2015 | Barouch et al. |
| D774,857 S | 12/2016 | Pendock |
| 9,914,227 B2 * | 3/2018 | Greadington ............. B67B 7/30 |
| D816,451 S | 5/2018 | Huseman et al. |
| D817,135 S | 5/2018 | Huesman et al. |
| 10,730,194 B2 | 8/2020 | Marble |
| 2003/0126747 A1 | 7/2003 | Kusaba |
| 2003/0167640 A1 | 9/2003 | Heck et al. |
| 2004/158269 A1 | 8/2004 | Holman |
| 2006/0196018 A1 | 9/2006 | Taylor et al. |
| 2007/0107232 A1 | 5/2007 | Green |
| 2013/0340263 A1 | 12/2013 | Votolato |
| 2014/0059865 A1 * | 3/2014 | Lin .......................... A01G 3/02 30/184 |
| 2014/0208594 A1 | 7/2014 | Scimone et al. |
| 2015/0033919 A1 | 2/2015 | Gingrich |
| 2018/0368333 A1 | 12/2018 | Dorton |
| 2020/0070261 A1 | 3/2020 | Gore |
| 2020/0084974 A1 | 3/2020 | Dorton |
| 2021/0251150 A1 * | 8/2021 | Dorton ..................... A01G 3/02 |

\* cited by examiner

ORIGINAL CLONE CUTTER

CROSS-REFERENCE TO RELATED APPLICATIONS

This application is a continuation-in-part of U.S. patent application Ser. No. 16/001,906 filed Jun. 6, 2018, which claims the benefit of U.S. Provisional Patent Application No. 62/603,625 filed Jun. 6, 2017, the entire contents of which are hereby incorporated by reference.

BACKGROUND

The following is a tabulation of some prior art that presently appears relevant:

U.S. Patents

| Pat. No. | Issue Date | Patentee |
| --- | --- | --- |
| 5,438,759 | 1995 Aug. 8 | Janice A. Dieringer |
| U.S. Pat. No. D485,014 S | 2004 Jan. 6 | Dal LaMagna and Mario Giampaoli |
| U.S. Pat. No. 8,984,754 B1 | 2015 Mar. 24 | Alexandre Rachid Kaidi and Hamid Reza Shamsapour |
| U.S. Pat. No. 8,429,825 B2 | 2013 Apr. 13 | James E. Johanson |
| 5,353,505 | 1994 Oct. 11 | Hidekazu Okada |
| 4,902,776 | 1978 Jun. 6 | William Ferguson |
| Des. 273,172 | 1984 Mar. 27 | Masami Yamagishi |
| U.S. Pat. No. D613,571 S | 2010 Apr. 13 | Wolfram Quante |
| 5,016,353 | 1991 May 21 | Clemens A Iten |
| 4,053,979 | 1977 Oct. 18 | Harlan L. Tuthill and John O. Freeborn |
| 5,711,075 | 1998 Jan. 27 | Jeffrey A. Wolf |
| U.S. Pat. No. 7,730,620 B1 | 2010 Jun. 8 | Christopher Anastasi |

Clones are cut from Mother Plants. The process for cutting clones today is time consuming and tedious. The process in which clones are cut today relies on using a scalpel or razor blade, both of which are ineffective.

When cutting with a razor blade or scalpel you must set the tool down which exposes the razor blade or scalpel to bacteria. Bacteria in turn can contaminate the clone.

When cutting a clone from a Mother Plant with a razor blade or scalpel you must pinch the top of the new clone and slightly pull up to allow the razor blade or scalpel to cut through the Mother Plant. During this process the cut is not precise.

Another problem with cutting clones with a razor blade or scalpel is if the first cut is done incorrectly, it is very difficult to make a second cut. In order to make a second cut, a clone must be placed on a sanitary cutting board and you must then attempt to push the blade back through.

Clone cutting, is done free-hand. Free-hand cutting is hard on the Mother Plant, her roots and the new clone's stem. The reason it is hard on them is because there is a jerking motion which may cause damage to the Mother Plant and her roots.

Finally, when using a razor blade or scalpel to cut clones there is a risk of injury. If the blade slips it is very easy to cut yourself.

Clone cutting is a very time consuming and tedious process which needs to remain sanitary, precise and safe throughout the process. The way clone cutting is done today is not the most effective or efficient process.

U.S. Pat. No. 5,438,759 to Dieringer, is a Button Removal Device. Although the device has the u-shaped housing, it is used to remove buttons from card stock.

U.S. Pat. No. D485,014 S to LaMagna and Giampaoli, is a Cuticle Nipper Tweezer. The Tweezer has the u-shaped housing; however, it is designed to nip cuticles.

U.S. Pat. No. 8,984,754 B1 to Kaidi and Shamsapour, is a Nail Clipper with Blade Insert. The Nail Clipper has the u-shaped housing and removal blade, it is designed to cut finger or toe nails.

U.S. Pat. No. 8,429,825 B2 to Johanson, is a Cutting Apparatus. The Cutting Apparatus has the u-shaped housing with a slot for the blade to push through to an activated position, with the cutting edge extending outwardly of the slot and guide. The Apparatus is used to cut various materials such as paperboard or corrugated paper.

U.S. Pat. No. 5,353,505 to Okada, is Grip Scissors. The Scissors have the u-shaped housing with two blades that slide past each other. The Grip Scissors are used for thread-cutting.

U.S. Pat. No. 4,092,776 to Ferguson, is a Cutting Tool. The Cutting Tool has the u-shaped housing with two blades which are able to crossover and clear said cutting surface.

U.S. Pat. No. Des. 273,172 to Yamagishi, is a Thread Nipper or The Like. The Thread Nipper has the u-shaped housing with two blades that crossover. The purpose of the Thread Nipper is thread-cutting.

U.S. Pat. No. D613,571 S to Quante, is a Cutting Implement. The Cutting Implement has the u-shaped housing with two crossover blades.

U.S. Pat. No. 5,016,353 to Iten, is a Suture Cutter. The Suture Cutter has the u-shaped housing with a blade that functions as a probe. It provides a suture cutter for cutting sutures in a skin surface.

U.S. Pat. No. 4,053,979 to Tuthill and Freeborn, is a Suture Cutter. The Suture Cutter has the u-shaped housing and removes surgical sutures with a slicing action.

U.S. Pat. No. 5,711,075 to Wolf, is a Unitarily Formed Plastic Soft Tissue Nipper. The Soft Tissue Nipper has the u-shaped housing with two blades at the end of each arm. The blades are required to be urged into abutting edge-to-edge contact. The purpose of the Soft Tissue Nipper is to be a hand-held tool for removing soft tissue, such as cuticles at base of fingernails.

U.S. Pat. No. 7,730,620 B1 to Anastasi, is a Plastic Package Opener. The Package Opener has the u-shaped housing with a blade member is mounted within the interior surface of an angled leg in order for the blade member to be directed across the surface of a plastic package.

The description of prior art all have the u-shaped housing, however, serve the purpose of something other than Clone Cutting.

SUMMARY

The present invention, The Original Clone Cutter, does not require using a scalpel to cut clones. The embodiment of the invention is a single blade mounted into the u-shaped housing that presses firmly against a flat surface. Only one blade is used, in order to not damage the fibers at the end of a cutting. Cutting clones with the present invention is not hard on the mother plant, her roots or the new clone's stem. The present invention cuts clones without the previous jerking motion caused by using a razor blade or scalpel free hand. There is not a need to pinch and pull up on the new clone stem which is required in prior methods of clone cutting. The present invention allows the blade to remain sanitized which allows for a clean, precise cut. The present invention allows for you to make multiple cuts with the same precision as the first in the circumstance you made your first cut incorrectly. The present invention has an easy squeeze function which allows for easy, safe use in either hand. It allows even the novice clone cutters ease of use.

Clone cutting is important in everyone's everyday life. Clone cutting is a huge industry. Having clones remain undamaged during the cutting phase is a huge breakthrough that will benefit the entire world. Cutting clones is important to the world because: almost all fruits and vegetables that are consumed around the world come from clones. Almost all plants, flowers and trees purchased around the world come from clones. Cloning is also important because most crops are harvested at the same time. In order to produce a crop in which all taste, smell, and look the same, you must use clones.

In a clone cutter with a single blade cutting mechanism of the type comprising a u-shaped housing, slider, removeable single blade, and a flat cutting surface for the single blade to cut against. The clone cutter with a single blade cutting mechanism wherein said body is composed of mold injected plastic. The clone cutter with a single blade cutting mechanism of wherein said body is a u-shaped housing. The u-shaped housing of wherein the top part of the u-shaped housing is a blade mounting block. The blade mounting block of the u-shaped housing includes a square groove for the single blade to fit into. The single blade has a blade mount that enables the single blade to sit in the blade mounting block. The u-shaped housing of wherein said body has a raised, flat cutting surface beneath the blade. The flat cutting surface of wherein said body is raised, the length extends the whole length of the blade and the width of the housing. The clone cutter with a single blade cutting mechanism of wherein said body houses a removeable single blade. The single blade of wherein said body is a blade with an injection mold encasing the top of the blade. The injection mold of wherein the injection mold has a raised notch on one end for the blade slider cover to keep blade securely in position. The blade slider cover may be molded through injection. The injection mold of wherein the body of the blade slider cover has a raised nub on top of the slider. The blade slider cover slides inside a slider groove in the u-shaped housing above the blade. The blade slider cover has a round indentation underneath that aligns with the notch on the injection mold of the single blade.

Method of using a clone cutter with single blade cutting mechanism: providing a clone cutter, providing a single blade and inserting the single blade into the clone cutter, pushing closed the slider so the single blade is securely in place, inserting mother plant into clone cutter, squeezing u-shaped housing closed, bringing the single blade down firmly against the flat cutting surface.

DETAILED DESCRIPTION

Figure 1:
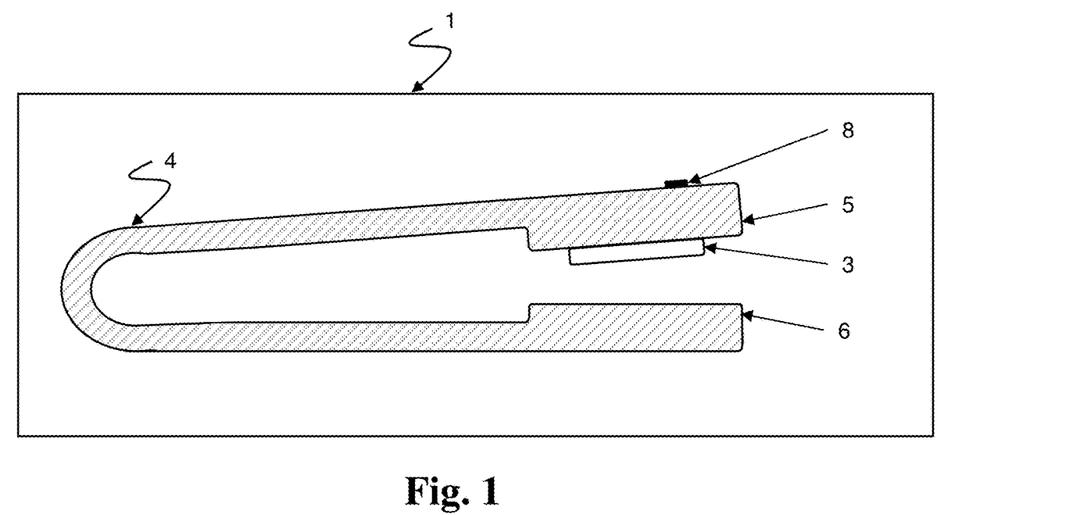
FIG. 1 is a side perspective illustration of the present invention.

FIG. 1 illustrates the present invention of the u-shaped housing 4, blade mounting block 5, and spacer-flat surface 6 are all one piece. A single blade 3 is used because a cutting needs to have one clean, precise cut. The single blade 3 is positioned from front to back, to provide the best angle to cut. It is important to only have one blade as having more than one blade to make a cutting, damages the fibers at the end of the cutting. The embodiment of the present invention is the u-shaped housing 4 was made for easy cleaning of the tool, having bacteria get onto the surface of the tool would contaminate the cutting. The u-shaped housing 4 is also used for ease of squeezing the tool with one free hand. The blade mounting block 5 is used to angle the u-shaped housing 4 to the angle the single blade 3 closes on the spacer-flat surface 6. The spacer-flat surface 6 closes at the same angle of the single blade 3.

Figure 2:
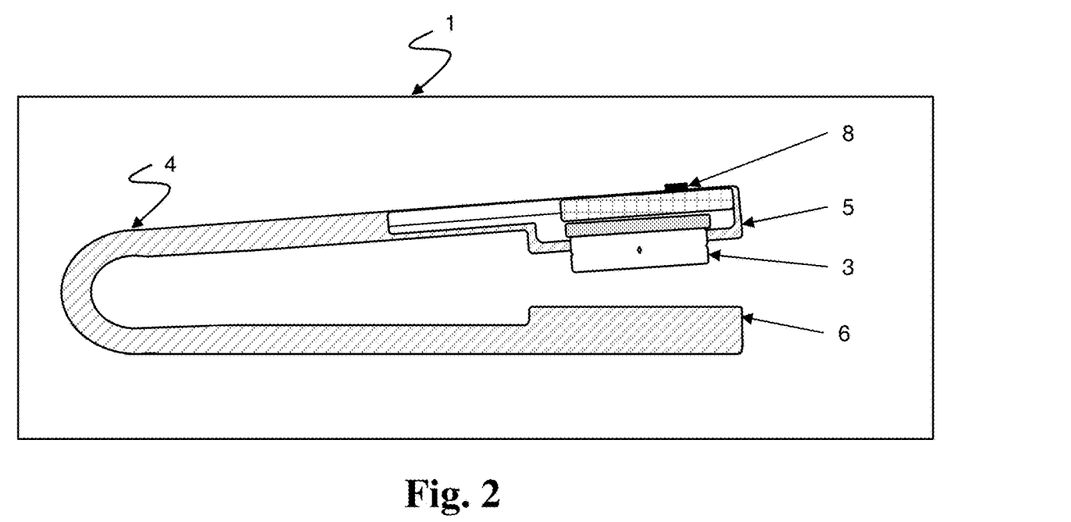
FIG. 2 is a cross-sectional side perspective illustration of the present invention with the single blade in the closed position.

FIG. 2 illustrates a cross-sectional side perspective of the present invention with the single blade in the closed position. The u-shaped housing 4, blade mounting block 5, and spacer-flat surface 6 are all one piece. The single blade 3 has a blade mount 9. The blade mount 9 of the single blade 3 sits in a square groove of the blade mounting block 5 of the u-shaped housing 4. The blade slide cover 7 slides back and forth on a slider groove. The blade slide cover 7 keeps the single blade 3 securely in place and slides back and forth for easy removal of the single blade 3. The slider nub 8 is in place to allow easy control of the blade slider cover 7.

Figure 3:
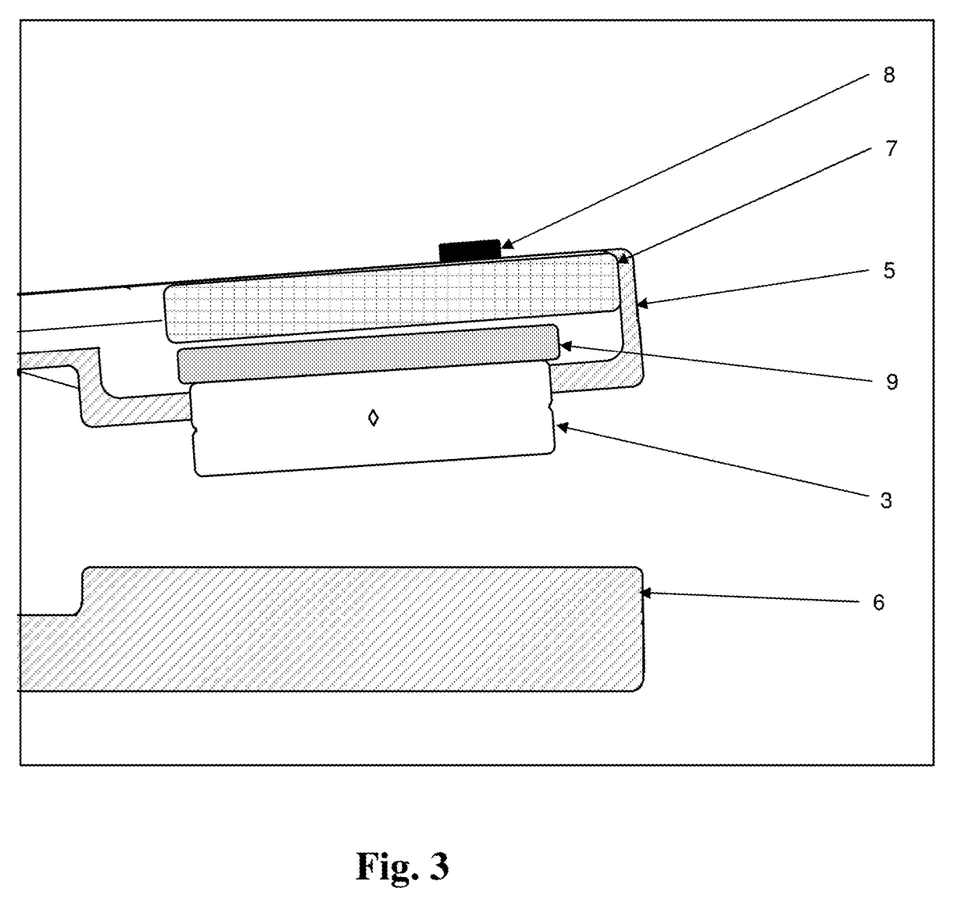
FIG. 3 is a close-up cross-sectional side perspective of the present invention with the single blade in the closed position.

FIG. 3 illustrates a close-up cross-sectional side perspective of the present invention with the single blade in the closed position. The u-shaped housing 4, blade mounting block 5, and spacer-flat surface 6 are all one piece. The single blade 3 has a blade mount 9. The blade mount 9 of the single blade 3 sits in a square groove of the blade mounting block 5 of the u-shaped housing 4. The blade slide cover 7 slides back and forth on a slider groove. The blade slide cover 7 is in the closed position securing the single blade 3 in place. The slider nub 8 is in place to allow easy control of the blade slider cover 7.

Figure 4:
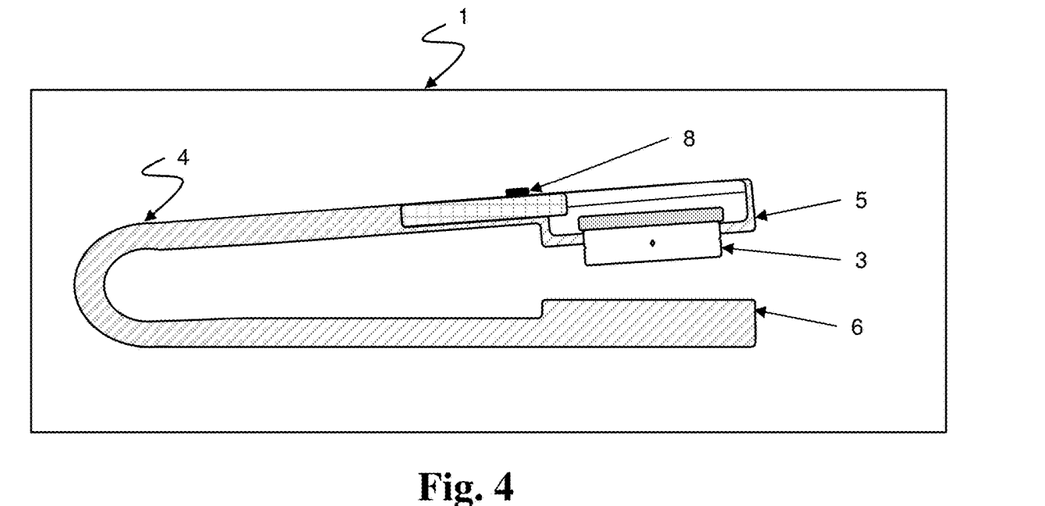
FIG. 4 is a cross-sectional side perspective illustration of the present invention with the single blade in the open position.

FIG. 4 illustrates a cross-sectional side perspective of the present invention with the single blade in the open position. The u-shaped housing 4, blade mounting block 5, and spacer-flat surface 6 are all one piece. The single blade 3 has a blade mount 9. The blade mount 9 of the single blade 3 sits in a square groove of the blade mounting block 5 of the u-shaped housing 4. The blade slide cover 7 slides back and forth on a slider groove. The blade slide cover 7 is in the open position allowing easy removal of the single blade 3. The slider nub 8 is in place to allow easy control of the blade slider cover 7.

Figure 5:
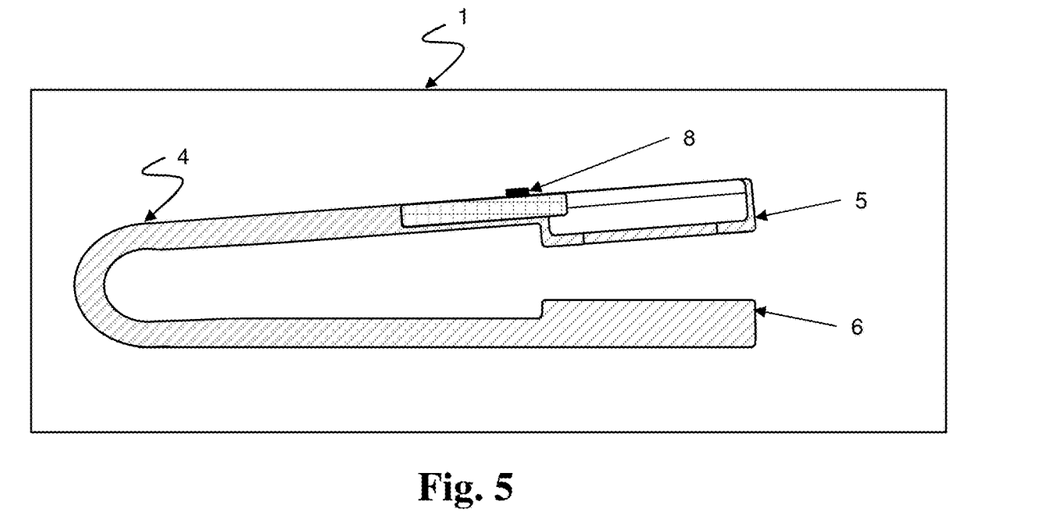
FIG. 5 is a cross-sectional side perspective illustration of the present invention in the open position.

FIG. 5 illustrates a cross-sectional side perspective of the present invention in the open position. The u-shaped housing 4, blade mounting block 5, and spacer-flat surface 6 are all one piece. The blade slide cover 7 slides back and forth on a slider groove. The slider nub 8 is in place to allow easy control of the blade slider cover 7.

Figure 6:
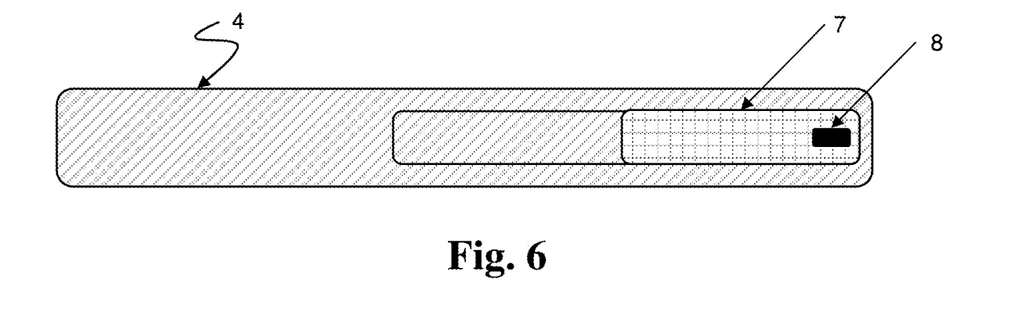
FIG. 6 is an over-head perspective illustration of the present invention in the closed position.

FIG. 6 is an over-head perspective illustration of the present invention in the closed position. The u-shaped housing 4 is one piece wherein the blade slider cover 7 has a raised slider nub 8 on top of the slider. The blade slider cover 7 slides inside a slider groove in the u-shaped housing 4 directly above the single blade 3. The blade slider cover 7 has a round indentation that aligns with the single blade 3.

Figure 7:
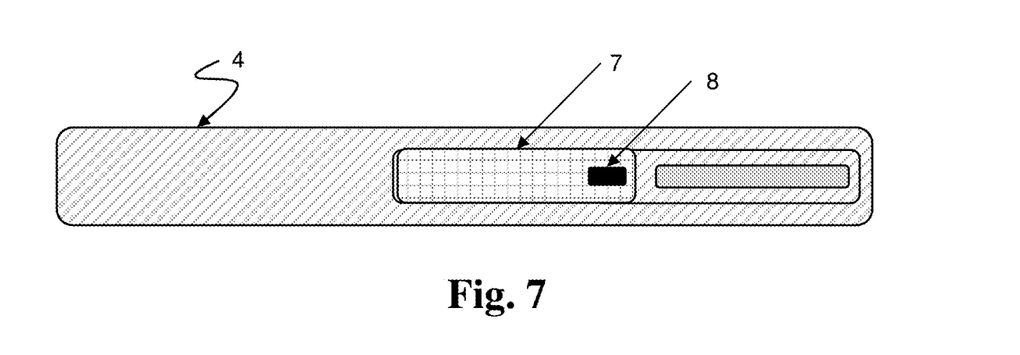
FIG. 7 is an over-head perspective illustration of the present invention with the single blade in the open position.

FIG. 7 is an over-head perspective illustration of the present invention with the single blade in the open position. The u-shaped housing 4 is one piece wherein the blade slider cover 7 has a raised slider nub 8 on top of the slider. The blade slider cover 7 slides inside a slider groove in the u-shaped housing 4 directly above the single blade 3. The blade slider cover 7 has a round indentation that aligns with the blade mount 9 of the single blade 3.

Figure 8:
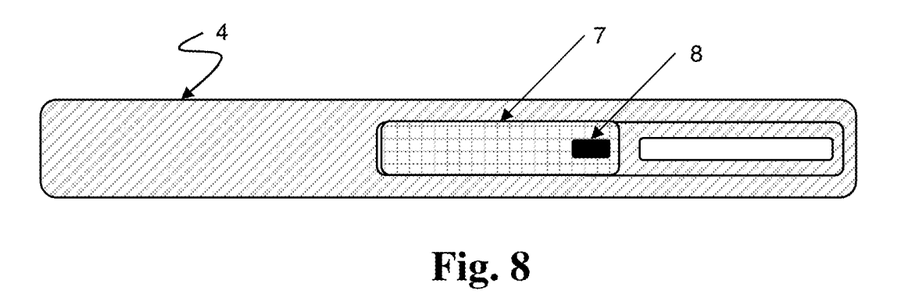
FIG. 8 is an over-head perspective illustration of the present invention in the open position.

FIG. 8 is an over-head perspective illustration of the present invention in the open position. The u-shaped housing 4 is one piece wherein the blade slider cover 7 has a raised slider nub 8 on top of the slider.

Figure 9:
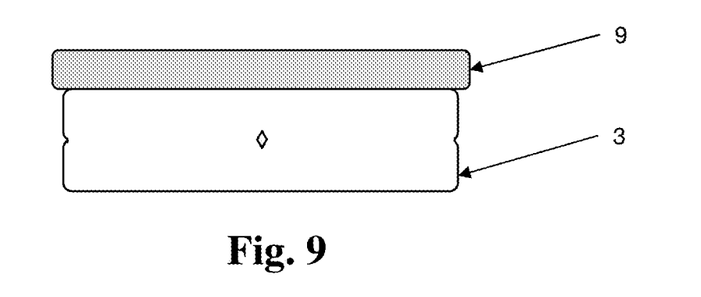
FIG. 9 is a side perspective illustration of the single blade of the present invention.

FIG. 9 illustrates the blade mount 9 on the single blade 3 that enables the single blade 3 to sit in the blade mounting block 5.

Figure 10:
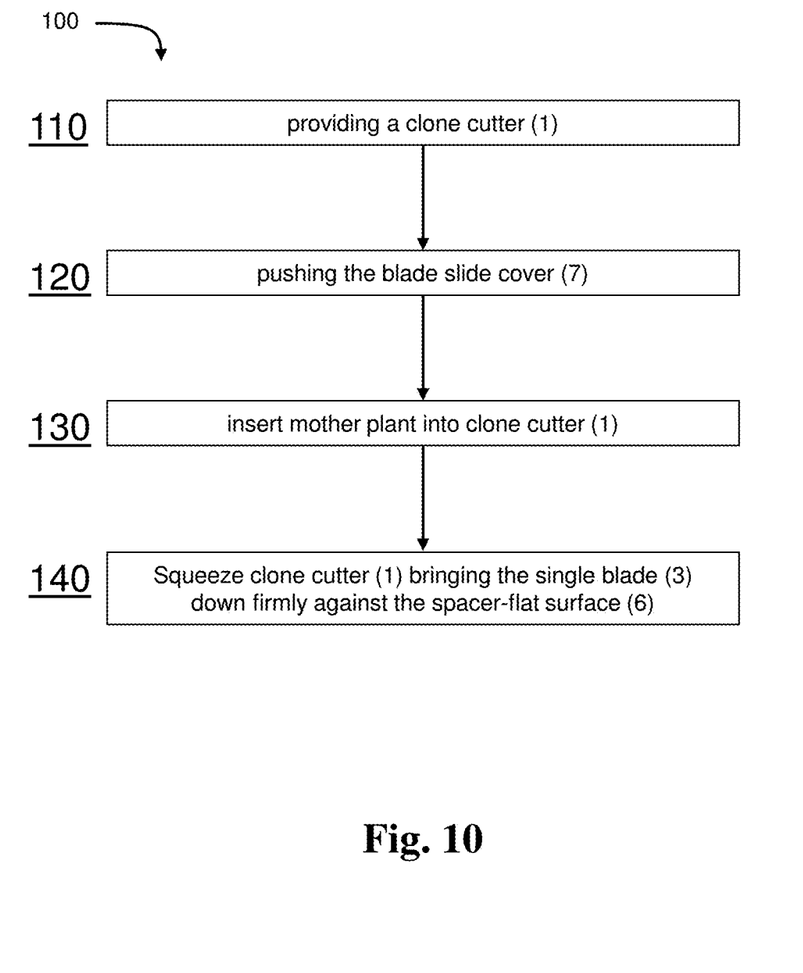
FIG. 10 is an illustration of an exemplary cutting sequence according to aspects of the present invention.

FIG. 10 is a flow diagram outline example method steps that can be carried out to use the clone cutter. The method steps can be implemented by any of the example means described herein.

Referring to a method 100 outlined in FIG. 10, in step 110 a clone cutter 1 can be provided. In step 120, a blade slide cover 7 can be pushed. In step 130, a mother plant can be inserted in the clone cutter 1. In step 140, the clone cutter 1 can be squeezed by bringing the single blade 3 down firmly against the spacer-flat surface 6.

ALTERNATIVE EMBODIMENTS

The present invention can have alternative embodiments. Alternative material can be used for the housing. Alternative material that would work for housing would be: fiberglass, plastic, ABS plastic, PVC Plastic, SCH 40 PVC, SCH 80 PVC Plastic, steel, stainless steel, harden steel, spring steel, aluminum or metal.

Alternative blade angles can be used. Alternative angles would be to insert the blade at a 45-degree angle or straight across. However, the blade will work at these angles the best angle is front to back.

The invention claimed is:

1. A clone cutter comprising:
a u-shaped housing with a first end portion and a second end portion each terminating in free ends, wherein the first end portion comprises:
a blade mounting block;
a recessed dado groove;
a single blade having a length and a width,
the single blade being sized to fit within the recessed dado groove, and
a blade slide cover with a slider nub that secures the single blade to the first end portion;
the second end portion comprises:
a spacer-flat surface on the second end portion opposite the single blade for the single blade to cut against.

2. The clone cutter of claim 1, wherein said u-shaped housing comprises one piece comprising mold injected plastic.

3. The clone cutter of claim of 1, wherein the spacer-flat surface of the second end portion of the u-shaped housing comprises a raised, flat cutting surface.

4. The clone cutter of claim 1, wherein the raised, flat cutting surface of the spacer-flat surface is at least the length of the single blade and aligned with the single blade.

5. The clone cutter claim 1, wherein the single blade is removeable from the first end portion of the u-shaped housing.

6. The clone cutter of claim 1, wherein the single blade is sized to fit within the recessed dado groove and beneath the blade slide cover while still permitting the single blade to extend from the blade mounting block.

7. The clone cutter of claim 1, wherein the blade slide cover is molded injected plastic.

8. The clone cutter of claim 1, wherein the blade slide cover of the first end portion of the u-shaped housing aligns with the single blade to secure the single blade within the first end portion.

9. Method of using a clone cutter with single blade cutting mechanism providing:
a clone cutter comprising
a u-shaped housing with a first end portion and a second end portion each terminating in free ends, wherein the first end portion comprises:
a blade mounting block;
a recessed dado groove;
a single blade having a length, a width, and a blade mount,
the single blade being sized to fit within the recessed dado groove and the blade mounting block, and
a blade slide cover with a slider nub that secure the single blade to the first end portion;
the second end portion comprises:
a spacer-flat surface on the second end portion opposite the single blade for the single blade to cut against,
pushing the blade slide cover so the single blade is securely in place,
insert mother plant between the first end portion and second end portion of the clone cutter,
squeeze u-shaped housing closed, bringing the single blade down firmly against the spacer-flat surface.

\* \* \* \* \*